US011672601B2

(12) United States Patent
Chu et al.

(10) Patent No.: US 11,672,601 B2
(45) Date of Patent: Jun. 13, 2023

(54) MEDICAL SYSTEMS, DEVICES, AND RELATED METHODS

(71) Applicant: Boston Scientific Scimed, Inc., Maple Grove, MN (US)

(72) Inventors: Michael S. H. Chu, Brookline, MA (US); Mayur K. Patel, Framingham, MA (US); Sacha Tang, Lowell, MA (US); Kimberly DeGraaf, Holden, MA (US)

(*) Notice: Subject to any disclaimer, the term of this patent is extended or adjusted under 35 U.S.C. 154(b) by 476 days.

(21) Appl. No.: 16/866,611

(22) Filed: May 5, 2020

(65) Prior Publication Data

US 2020/0352650 A1    Nov. 12, 2020

Related U.S. Application Data

(60) Provisional application No. 62/844,801, filed on May 8, 2019.

(51) Int. Cl.
| A61B 18/26 | (2006.01) |
| A61B 17/00 | (2006.01) |
| A61B 17/22 | (2006.01) |
| A61B 18/00 | (2006.01) |

(52) U.S. Cl.
CPC .... *A61B 18/26* (2013.01); *A61B 2017/00486* (2013.01); *A61B 2017/00902* (2013.01); *A61B 2017/22079* (2013.01); *A61B 2018/00505* (2013.01); *A61B 2218/007* (2013.01)

(58) Field of Classification Search
CPC .......... A61B 18/26; A61B 2017/00486; A61B 2017/00902; A61B 2017/22079; A61B 2018/00505; A61B 2218/007; A61B 2217/005; A61B 1/00094; A61B 1/00101; A61B 1/00137; A61B 1/0014; A61B 1/018; A61B 2018/00982; A61B 2018/00511; A61M 1/3695

See application file for complete search history.

(56) References Cited

U.S. PATENT DOCUMENTS

| 4,920,953 | A | * | 5/1990 | McGown ........... | A61B 1/00137 600/154 |
| 5,241,990 | A | * | 9/1993 | Cook ................. | A61B 18/1482 604/32 |
| 7,104,983 | B2 | | 9/2006 | Grasso, III et al. | |
| 9,936,963 | B2 | | 4/2018 | Batchelor et al. | |
| 10,085,759 | B2 | | 10/2018 | Ciulla | |

(Continued)

FOREIGN PATENT DOCUMENTS

EP    1 721 567    11/2006

OTHER PUBLICATIONS

International Search Report and Written Opinion issued in International Application No. PCT/US2020/031405, dated Jun. 26, 2020 (15 pages).

*Primary Examiner* — Richard G Louis

(57) ABSTRACT

A medical system may include an insertion device including a delivery shaft with at least one lumen, a tube coupled to an exterior of the delivery shaft, and an adaptor coupling a distal end of the delivery shaft to a distal end of the tube. One of the delivery shaft and the tube may be configured to receive an energy delivery device, and the other of the delivery shaft and the tube may be configured to be coupled to a suction source to apply suction.

17 Claims, 9 Drawing Sheets

(56) References Cited

U.S. PATENT DOCUMENTS

| | | | |
|---|---|---|---|
| 2003/0130564 A1* | 7/2003 | Martone | A61B 1/00071 600/139 |
| 2008/0249357 A1* | 10/2008 | Soetermans | A61B 1/00105 600/114 |
| 2009/0192350 A1* | 7/2009 | Mejia | A61B 1/267 600/109 |
| 2010/0016659 A1 | 1/2010 | Weitzner | |
| 2016/0158423 A1 | 6/2016 | Pigazzi | |
| 2016/0228113 A1* | 8/2016 | Weitzner | A61B 1/00087 |
| 2016/0317167 A1 | 11/2016 | Ben Muvhar | |
| 2016/0374700 A1* | 12/2016 | Olden | A61B 1/00101 606/106 |
| 2017/0215899 A1 | 8/2017 | Harrah et al. | |
| 2017/0333614 A1 | 11/2017 | Gao et al. | |
| 2017/0348015 A1 | 12/2017 | Behl | |
| 2018/0125515 A1 | 5/2018 | Jenkins et al. | |

* cited by examiner

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/844,801, filed May 8, 2019, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for removing hardened masses from a body lumen, for example, for performing a laser lithotripsy procedure with stone dusting.

BACKGROUND

Lithotripsy is a medical procedure involving the physical disruption of a hardened mass within a body cavity, such as kidney stones, gallstones, pancreatic stones, or the like. In such procedures, energy is applied to the hardened mass. Different energy sources may be used, such as electric, hydraulic, laser, mechanical, ultrasound, or the like. In laser lithotripsy, pulsed light energy from an energy delivery device may be converted into a mechanical energy in the form of a cavitation bubble associated with the occurrence of a shock-wave. This mechanical energy may facilitate disruption and/or breaking up of the hardened mass.

Many lithotripsy procedures generate particles or pollution within the body cavity as the hardened mass is disrupted and broken-up. For stone-like masses, these particles may be referred to as "stone dust." In laser lithography procedures, this stone dust may hinder visualization of the mass, which may prevent the physician from locating the mass and delivering the laser energy in the most efficient manner. Fluid may be injected into the body cavity so that a portion of the stone dust will naturally drain out of the body cavity with the fluid. However, stone dust or other particles may not drain out of certain body cavities or portions of a body cavity, for example, a lower pole of a kidney. Suction may be delivered to the body cavity to help remove the stone dust, but applying suction may require either removing the energy delivery device or inserting an additional medical device into the body cavity, which may prolong the procedure or expose the patient to contamination or other risks. Furthermore, the suction device may be susceptible to clogs or reduced fluid flow if stone dust or other particles accumulate within the suction lumen or if larger stones or particles enter the suction lumen. The aforementioned risks may increase the cost, time, and necessary personnel for a medical procedure, further complicating and prolonging the procedure, and exposing the patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, a medical system may include an insertion device including a delivery shaft with at least one lumen, a tube coupled to an exterior of the delivery shaft and including a lumen, and an adaptor coupling a distal end of the delivery shaft to a distal end of the tube. One of the delivery shaft and the tube may be configured to receive an energy delivery device, and the other of the delivery shaft and the tube may be configured to be coupled to a suction source to apply suction.

The medical system may include one or more of the following features. A central longitudinal axis of the lumen of the tube may be parallel to a central longitudinal axis of a lumen of the delivery shaft. The adaptor may include a first lumen coupled to the lumen of the tube, and the adaptor may include a second lumen coupled to the lumen of the delivery shaft. The first lumen of the adaptor may be connected to the second lumen of the adaptor via at least one aperture. The aperture may include a screen, a mesh, a strainer, a sieve, a filter, or a sifter. The aperture may include an opening that is smaller than a cross-sectional area of one of the lumen of the tube or the lumen of the delivery shaft, and the tube may include one or more fluid delivery openings located proximal to a coupling with the adaptor. At least one lumen of the adaptor may include a proximally tapered cross-section. The tube may be coupled to the delivery shaft via an outer sheath. The tube may be coupled to the delivery shaft via an adhesive. The adaptor may be coupled to the distal ends of the delivery shaft and the tube via a friction fit. The delivery shaft may include a visualization device. The adaptor may include a visualization opening at least partially aligned with the visualization device. The adaptor may be formed of an at least partially transparent material. The medical system may further include a retrieval device configured to be positioned within either the lumen of the delivery shaft or the lumen of the tube. The medical system may further include an end cap with a filter portion and an opening.

In another aspect, an adaptor for a medical system may include a first coupling portion configured to couple a tube to a first lumen of the adaptor, a second coupling portion configured to couple a delivery shaft to a second lumen of the adaptor, and an aperture fluidly connecting the first lumen to the second lumen. The first lumen and the second lumen may be parallel.

The adaptor for a medical system may include one or more of the following features. The first lumen may include a closed distal end, and the second lumen may include an open distal end defining a cavity. The cavity of the second lumen may be proximally tapered, and a proximal portion of the cavity may be adjacent to the aperture.

In a further aspect, a method may include coupling a distal end of a delivery shaft to a distal end of a tube via an adaptor, delivering the delivery shaft, the tube, and the adaptor to a body cavity, applying suction to the body cavity through a lumen of the delivery shaft or a lumen of the tube to remove an object via an aperture within the adaptor or to retain the object adjacent to the aperture within the adaptor, and delivering energy to the body cavity through the lumen of the delivery shaft or the lumen of the tube.

The method may include one or more of the following features. The step of delivering the delivery shaft, the tube, and the adaptor to the body cavity may include positioning a guidewire within the lumen of at least one of the delivery shaft or the tube and advancing at least one of the delivery shaft, the tube, and the adaptor along the guidewire. The step of delivering energy to the body cavity may further include applying suction to the body cavity. The method may further include repositioning the delivery shaft, the tube, and the adaptor to another position within the body cavity and repeating the apply suction step and the energy delivery step.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," "generally," and "approximately," indicate a range of values within +/−10% of a stated value.

BRIEF DESCRIPTION OF THE DRAWINGS

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems, devices, and methods to facilitate and improve the efficacy, efficiency, and safety of medical procedures to break up and remove hardened masses. For example, aspects of the present disclosure may provide an operator (e.g., a physician, medical technician, or other medical service provider) with the ability to more easily apply laser energy from an energy source to a kidney stone and apply suction to remove stone dust. Aspects of the present disclosure may allow an operator to deliver energy and apply suction within a body cavity to remove small stones or stone dust, and breakup larger stones to be removed without the need to remove medical devices from the body cavity. Moreover, aspects of the present disclosure may allow an operator to collect stone dust or stone fragments at a distal end of the medical device and remove the collected stone dust or stone fragments from the body cavity. Additionally, aspects of the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
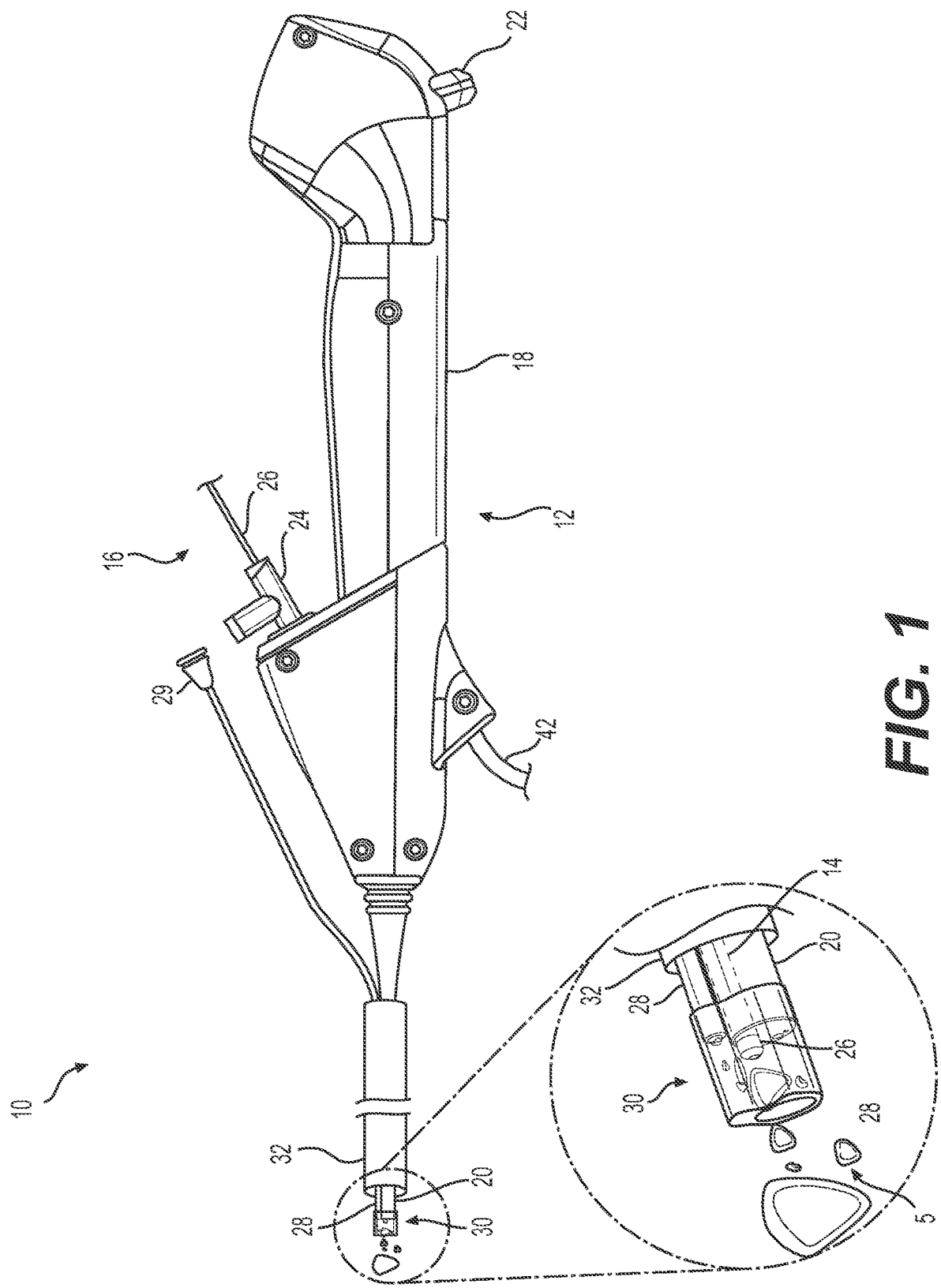
FIG. 1 illustrates a medical system according to aspects of the present disclosure.

FIG. 1 illustrates a medical system 10 that includes an insertion device 12 with at least one lumen 14, and a medical device 16. Insertion device 12 may include a body 18 and a delivery shaft 20. Body 18 may include a deflection lever 22 and at least one port 24. The at least one lumen 14 passes through delivery shaft 20 and may be fluidly coupled to port 24. Medical device 16 may include an energy delivery device 26, e.g., a laser fiber. The energy delivery device 26 may be coupled to insertion device 12 and may be inserted through port 24 and the at least one lumen 14 such that energy may be delivered from a distal end of energy delivery device 26 positioned at, or distal of, a distal end of delivery shaft 20. Medical system 10 also includes a tube 28. Tube 28 may be positioned adjacent to and/or along delivery shaft 20. Tube 28 may include a hub 29 coupled to one or more of a suction source, a collection bag, a retrieval device, etc. A distal end of tube 28 may be coupled to insertion device 12 via an adaptor 30. For example, adaptor 30 may be coupled to distal ends of delivery shaft 20 and tube 28, and may help direct suction and energy from energy delivery device 26 to break up and remove stones 5. In some arrangements, tube 28 may also be coupled to delivery shaft 20 via a sheath 32. That is, a lumen of sheath 32, within which delivery shaft 20 and tube 28 may be received, may be sized or configured so as to secure at least a portion of tube 28 to with at least a portion of delivery shaft 20.

Insertion device 12 may be a ureteroscope (e.g., LithoVue™ Single-Use Digital Flexible Ureteroscope by Boston Scientific Corp.), an endoscope, a hysteroscope, a bronchoscope, a cystoscope, or any similar device. Insertion device 12 may be for single-use and be disposable, or insertion device 12 may be reusable. Deflection lever 22 may be used to deflect and/or position a distal portion of delivery shaft 20, along with tube 28 and adaptor 30. The at least one port 24 may be a T-connector as shown in FIG. 1, may be a Y-connector, or another appropriate connector. Port 24 may be threaded, may be a luer component, and/or may include one or more internal flexible seals. The at least one port 24 may connect to lumen 14 in delivery shaft 20 through at least one internal lumen (not shown) in the body 18 of insertion device 12.

Figure 2:
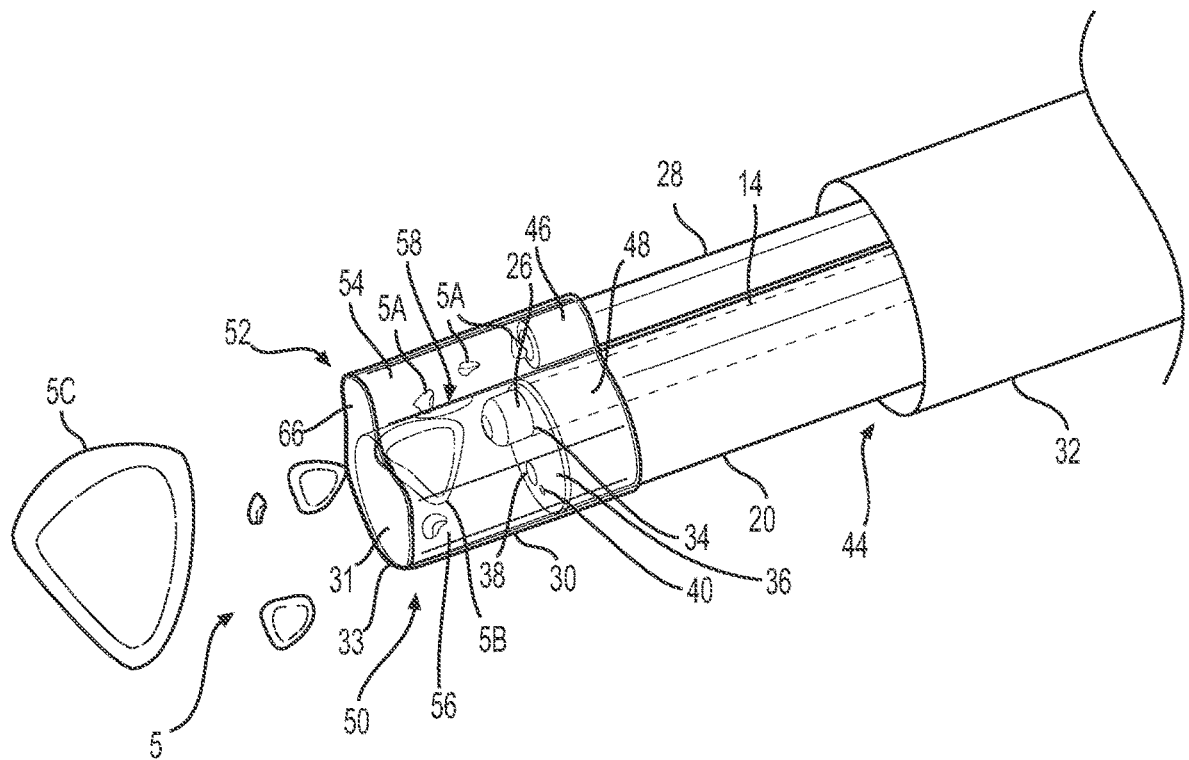
FIG. 2 illustrates a distal portion of the medical system of FIG. 1, according to aspects of the present disclosure.

As shown in FIG. 2, lumen 14 terminates in a distal opening 34. Opening 34 may be arranged in a distal end 36 of delivery shaft 20, and may fluidly connect to port 24 to form a working channel. Accordingly, energy delivery device 26 may be inserted through port 24 and extended to a position just proximal to distal end 36, flush with distal end 36, or extended distally beyond distal end 36. Delivery shaft 20 may include an integral camera 38 and/or an illumination source 40 at distal end 36, which may be connected to a user interface and a display via a communication and power conduit 42 (FIG. 1) extending from body 18 of insertion device 12.

As noted previously, optionally, tube 28 may also be coupled to delivery shaft 20 via sheath 32, and internal lumens of tube 28 and delivery shaft 20 may be substantially parallel. That is, a central longitudinal axis of delivery shaft 20 may be parallel to a central longitudinal axis of tube 28. Sheath 32 may be an access sheath or other appropriate sheath. Tube 28 may be longitudinally fixed relative to delivery shaft 20. Alternatively, the coupling via sheath 32 may allow tube 28 to be longitudinally movable relative to delivery shaft 20. Additionally, in one aspect, sheath 32 may allow fluid to be delivered distally in an area, cavity, or channel 44 radially between sheath 32 and delivery shaft 20 or radially between sheath 32 and tube 28. For example, while applying suction to a body cavity during a procedure to proximally remove fluid, stone dust, and other particles, a user may also (e.g., simultaneously) deliver irrigation fluid or other fluids distally via channel 44 in order to maintain an appropriate pressure within the body cavity and/or promote fluid flow and/or visualization within the body cavity.

As mentioned, adaptor 30 may be coupled to a distal end 36 of delivery shaft 20 and tube 28, and thus couple delivery shaft 20 to tube 28. For example, adaptor 30 may include a first coupling or a tube coupling 46 with an opening sized to receive and/or be coupled to a distal end of tube 28. Adaptor 30 may also include a second coupling or a shaft coupling 48 with an opening sized to receive and/or be coupled to distal end 36 of delivery shaft 20. Tube coupling 46 and shaft coupling 48 may couple adaptor 30 to tube 28 and delivery shaft 20 via a friction fit. Tube coupling 46, shaft coupling 48, tube 28, and delivery shaft 20 may include respective shapes and sizes to help ensure a friction fit. For example, tube coupling 46 may include an inner diameter similar to or slightly larger than an outer diameter of tube 28. Alternatively or additionally, adaptor 30 may be coupled to tube 28 and/or delivery shaft 20 via an adhesive or one or more loops or rings of material (e.g., an elastic material, a heat-shrink material, etc.). The adhesive or loops of material may surround portions of adaptor 30, tube 28, and delivery shaft 20 in order to aid in the coupling. In one aspect, tube 28 may be coupled to adaptor 30 via an adhesive, and delivery shaft 20 may be coupled to adaptor 30 via a friction fit, which may allow for a quick and/or easy assembly of system 10 without requiring manipulation of tube 28. Adaptor 30 may form a cavity 31 to receive and/or treat stones 5 or other hardened masses.

In one aspect, adaptor 30 may include a substantially cylindrical portion 50 with a protrusion 52. Cylindrical portion 50 of adaptor 30 may include a radial cross-section similar to delivery shaft 20, and protrusion 52 may include a radial cross-section similar to tube 28. The shape of adaptor 30 may help couple delivery shaft 20 and tube 28 without significantly increasing a cross-sectional size of adaptor 30 or the distal end of medical system 10.

Tube coupling 46 and shaft coupling 48 may form respective lumens, for example, a first lumen or a tube coupling lumen 54 and a second lumen or a shaft coupling lumen 56. Tube coupling lumen 54 may include an open proximal end in order to be coupled to and fluidly connect to tube 28. In one aspect, tube coupling lumen 54 may include a distal end 66 that is closed. That is, tube coupling lumen 54 may terminate proximally of a distalmost end of adaptor 30. Alternatively, and as discussed with respect to FIGS. 5-7, distal end 66 of tube coupling lumen 54 may be open (e.g., a through-lumen), which may allow for a retrieval device to be inserted through tube 28 and extended out of the open distal end, for example, to retrieve or reposition a stone 5 before a stone dusting procedure is performed or during a stone dusting procedure. Shaft coupling lumen 56 may include an open proximal end in order to be coupled to delivery shaft 20. Shaft coupling lumen 56 may also include an open distal end in order to receive fluid, stone dust 5A, stones 5, or other particles.

Tube coupling lumen 54 and shaft coupling lumen 56 may be substantially parallel within adaptor 30 and may be connected via an aperture 58. Aperture 58 may be sized or shaped to control or limit the size of stone dust 5A or other particles received within tube coupling lumen 54 and drawn (e.g., sucked) proximally by the application of suction from a suction source coupled to a proximal end of tube 28 (e.g., via hub 29). For example, suction may be delivered through tube 28 to draw stones 5 toward adaptor 30 and into cavity 31. Smaller stones or stone dust 5A may be small enough pass through aperture 58 and travel proximally through tube 28 to be removed from the body cavity. Large stones 5B or clumps of stone dust 5A that are not small enough to pass through aperture 58 may be held or retained by the suction against aperture 58. A user may move or deflect medical system 10 in order to move the retained large stones 5B or clumps of stone dust 5A, for example, to a different location in a kidney where energy delivery may be safer and/or more effective. Even larger stones 5C or clumps of stone dust 5A that are not small enough to pass into cavity 31 may be held or retained by the suction against a distal face or rim 33 of adaptor 30. A user may then move or deflect medical system 10 in order to move the retained even larger stones 5C or clumps of stone dust 5A, for example, to a different location in the kidney where energy delivery may be safer and/or more effective.

In one aspect, when in the retained position within adaptor 30, the large stones 5B or clumps of stone dust 5A are aligned with a distal end of the energy delivery device 26. Accordingly, energy delivery device 26 may be used to apply energy to the large stones 5B or clumps of stone dust 5A to further fragment and/or break up the large stones 5B or clumps of stone dust 5A in order for the large stones 5B or stone dust 5A to pass through aperture 58 and proximally through tube 28 for removal. Energy delivery device 26 may also be extended distally into or through cavity 31 and/or distally beyond adaptor 30. In this aspect, energy delivery device 26 may be used to apply energy to the even larger stones 5C or clumps of stone dust 5A to fragment and/or break up the even larger stones 5C or clumps of stone dust 5A in order for the even larger stones 5C or stone dust 5A to pass into cavity 31 and/or through aperture 58 and proximally through tube 28 for removal. Moreover, aperture 58 may help to prevent large stones 5B or stone dust 5A from clogging tube 28. In one aspect, aperture 58 may further include a passive barrier, such as, for example, a screen, a mesh, a strainer, a sieve, a filter, a sifter, etc. Additionally, adaptor 30 may include more than one aperture 58 (FIG. 9B), and a size and/or shape of aperture 58 may be varied (FIG. 9C) in order to control and/or direct the flow of stone dust 5A into tube 28.

Figure 8:
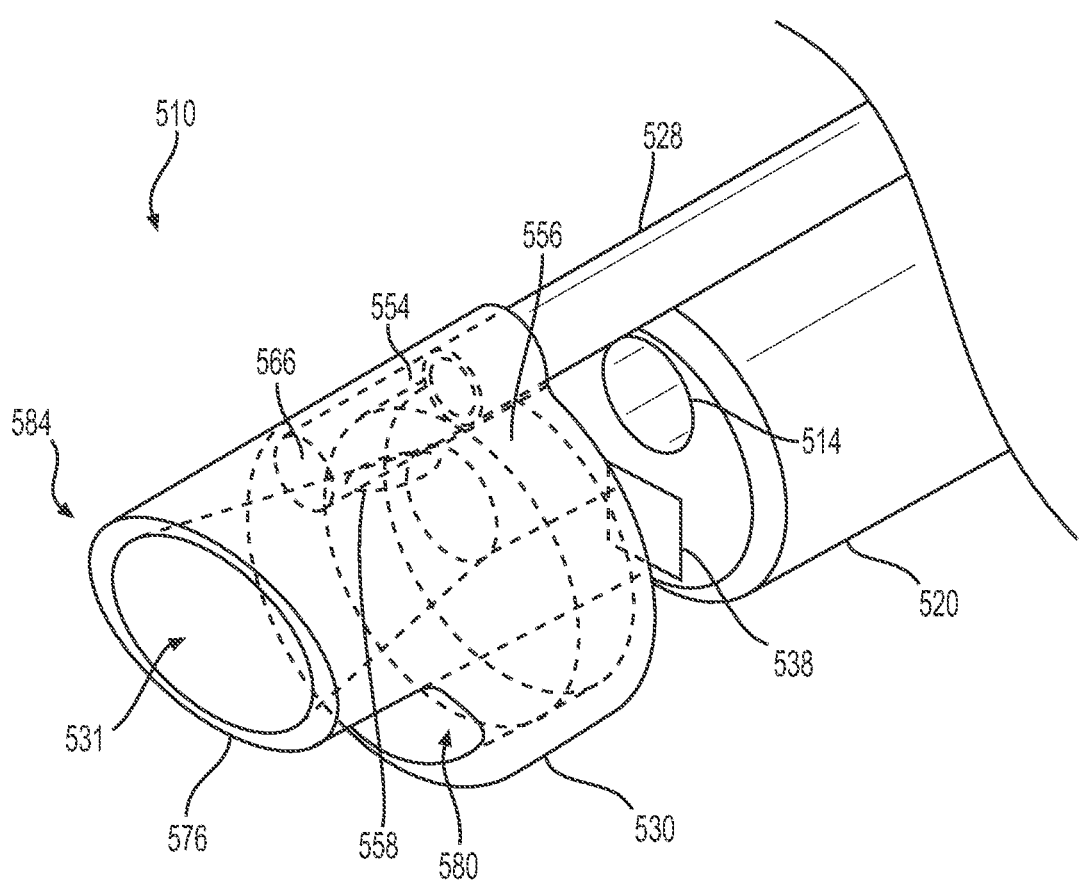
FIG. 8 illustrates a partially exploded view of a distal portion of an additional exemplary medical system, according to aspects of the present disclosure.

As discussed in detail with respect to FIG. 8, shaft coupling lumen 56 and/or cavity 31 may also include a tapered portion, funnel-shaped portion, or cup-shaped portion. The tapered portion may be formed in a distal portion of adaptor 30, and may include a larger distal opening and a smaller proximal opening. That is, a cross-sectional dimension of shaft coupling lumen 56 may narrow or taper proximally. For example, the distal opening may include a cross-sectional size similar to the cross-section of delivery shaft 20, and the proximal opening may be approximately the same size as lumen 14 and/or energy delivery device 26.

In one aspect, when applying suction through tube 28, the suction may be applied through tube 28, tube coupling lumen 54, aperture 58, shaft coupling lumen 56, and cavity 31, including the tapered portion, in order for the suction to be applied to an area distal of medical system 10. Accordingly, stones 5 or stone dust 5A may be drawn into cavity 31, and the tapered portion may help direct the smaller stones 5 or stone dust 5A toward aperture 58 and/or direct large stones 5B to a position aligned with the distal end of energy delivery device 26. Furthermore, the tapered portion may help to direct the fluid within the body cavity that helps carry the stones 5, stone dust 5A, and other material toward aperture 58.

Adaptor 30 may be formed of a polymer, for example, a polymer that is transparent so as to not inhibit a visualization device coupled to the distal end of delivery shaft 20. In this aspect, adaptor 30 may be coupled to insertion device 12, and a visualization device on the distal end of delivery shaft 20 (e.g., camera 38) may be used to locate one or more stones 5 and to position delivery shaft 20 during the procedure. Additionally or alternatively, adaptor 30 may be formed by additive manufacturing or another appropriate formation process.

Figure 3:
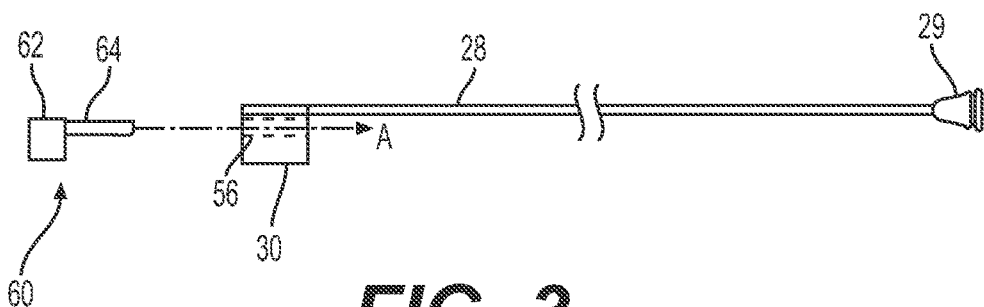
FIG. 3 illustrates a tube and an adaptor of the medical system of FIG. 1 and an alignment tool that may be used with the medical system of FIG. 1, according to aspects of the present disclosure.

As shown in FIG. 3, adaptor 30 may be coupled to tube 28 and delivery shaft 20 via an alignment tool 60. Alignment tool 60 may include a base 62 and a shaft 64. Base 62 may be approximately the same size and shape as a distal face of adaptor 30. For example, base 62 may include a size and shape that matches the size and shape of cylindrical portion 50 and protrusion 52. Shaft 64 may be sized to extend through shaft coupling lumen 56 of adaptor 30. Shaft 64 may also be sized to extend through shaft coupling lumen 56 and into a portion of lumen 14 (FIG. 2) of delivery shaft 20. For example, shaft 64 may include an outer diameter that is smaller than an inner diameter of shaft coupling lumen 56 and an inner diameter of lumen 14. Shaft 64 may be inserted in direction A into both shaft coupling lumen 56 and lumen 14. Accordingly, alignment tool 60 may help to align tube coupling lumen 54 with tube 28 and to align shaft coupling lumen 56 with lumen 14 in order to ensure that fluid, stones 5, and/or stone dust 5A may be delivered to tube 28, and that the distal end of energy delivery device 26 may be able to extend into shaft coupling lumen 56 and apply energy to larger stones 5B. Additionally, alignment tool 60 may help to align lumen 14 with aperture 58 such that, when energy delivery device 26 is extended through lumen 14 and into cavity 31, energy delivery device 26 may be aligned with one or more large stones 5B or clumps of stone dust 5A that are held against aperture 58.

As mentioned, distal end 66 of tube coupling lumen 54 may be closed or opened. When distal end 66 of tube coupling lumen 54 is closed, any suction or negative pressure delivered through tube 28 may be directed toward aperture 58. When distal end 66 of tube coupling lumen 54 is open, a user may deliver a medical device (e.g., an expandable basket or other retrieval device) through tube 28, through tube coupling lumen 54 of adaptor 30, and out of the open distal end 66. For example, the medical device may be used to capture or move one or more stones 5. In one aspect, the opening in distal end 66 may be smaller than the internal lumen of tube 28, which may help to prevent material entering lumen 28 through the opening and clogging the lumen of tube 28. Furthermore, tube coupling lumen 54 may taper distally to the smaller distal opening, which may help direct or guide the medical device toward the opening.

Figure 4A:
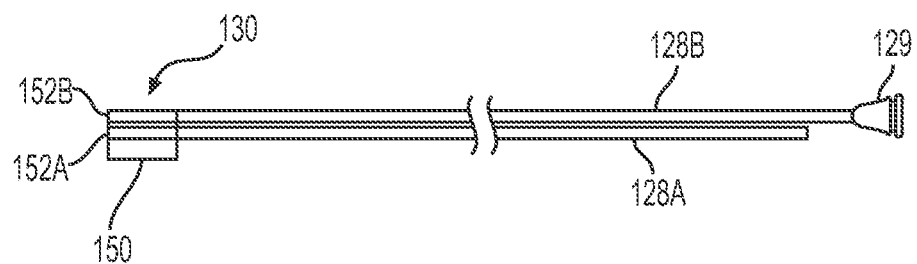
FIG. 4A illustrates a top view of tubes and an adaptor that may be incorporated in a medical system.
Figure 4B:
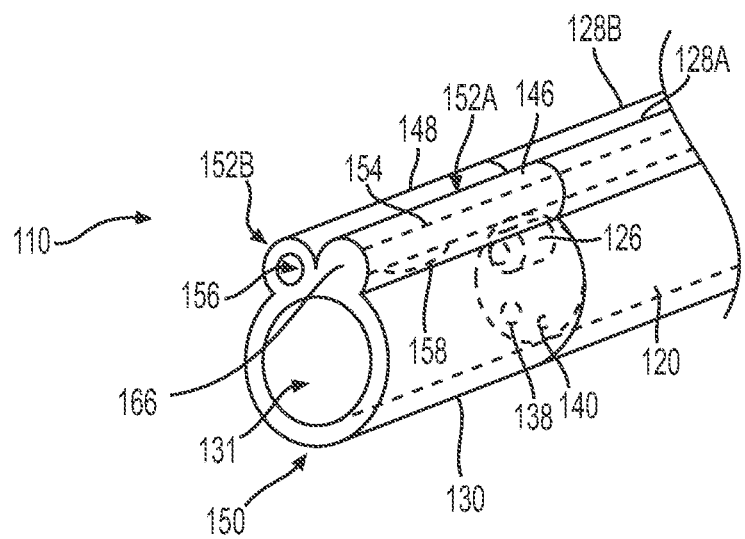
FIG. 4B illustrates a perspective view of the tubes and adaptor coupled to an insertion device, according to aspects of the present disclosure.

FIGS. 4A and 4B illustrate an alternative example according to the present disclosure, with similar elements to medical system 10 shown by 100 added to the reference numbers. As shown in FIGS. 4A and 4B, medical device 116 may include two tubes 128A, 128B and an adaptor 130. FIG. 4A is a top view of tubes 128A, 128B. Tubes 128A, 128B may be secured to a delivery shaft, such as delivery shaft 20 of FIG. 1. For example, tubes 128A, 128B may be secured to a delivery shaft (e.g., delivery shaft 20) via an adhesive. Tube 128A may be used to apply suction, as discussed above with respect to tube 28. Tube 128B may be used to deliver irrigation fluid, for example, via a proximal irrigation source. Tube 128B is shown coupled to a proximal hub 129, but it is noted that a proximal end of tube 128A may also be coupled to a hub, as in FIG. 1. That is, a first hub 129 may be coupled to a proximal end of tube 128A and a second hub 129 may be coupled to a proximal end of tube 128B. Because tubes 128A, 128B are coupled to the delivery shaft via an adhesive, and because tube 128B may deliver irrigation fluid to the body cavity, a sheath may not be necessary, which may reduce the overall profile of medical system 110. In one aspect, tubes 128A, 128B may be coupled to adaptor 130 via an adhesive, and delivery shaft 120 may be coupled to adaptor 130 via a friction fit. Additionally, as shown in FIG. 4A, tubes 128A, 128B may be aligned with respective protrusions 152A, 152B, which include first and second lumens 154, 156, respectively, as shown and discussed below with respect to FIG. 4B.

As shown in FIG. 4B, adaptor 130 may include a cylindrical portion 150 and two protrusions 152A, 152B. Protrusions 152A, 152B may include first and second couplings 146, 148 with first and second lumens 154, 156, respectively. First tube 128A may be coupled to first lumen 154 via first coupling 146, and second tube 128B may be coupled to second lumen 156 via second coupling 148. In this aspect, adaptor 130 may include an aperture 158 connecting first lumen 154 to a cavity 131 within cylindrical portion 150. First lumen 154 may include a closed distal end 166 in order to direct the applied suction through aperture 158. Second lumen 156 may include an open distal end in order to deliver irrigation fluid distally into the body cavity and to allow one or more medical devices to be delivered to the body cavity through second tube 128B and second lumen 156. Although not shown, adaptor 130 may also include a connection from tube 128B to the interior cavity 131 or to a distal face of delivery shaft 120 in order for the irrigation fluid to help remove and/or flush material from an area around energy delivery device 126, camera 138, and/or illumination source 140. In another aspect, irrigation fluid may be delivered through the working channel of delivery shaft 120 to help remove and/or flush material from the area around energy delivery device 126, camera 138, and/or illumination source 140.

Figure 5:
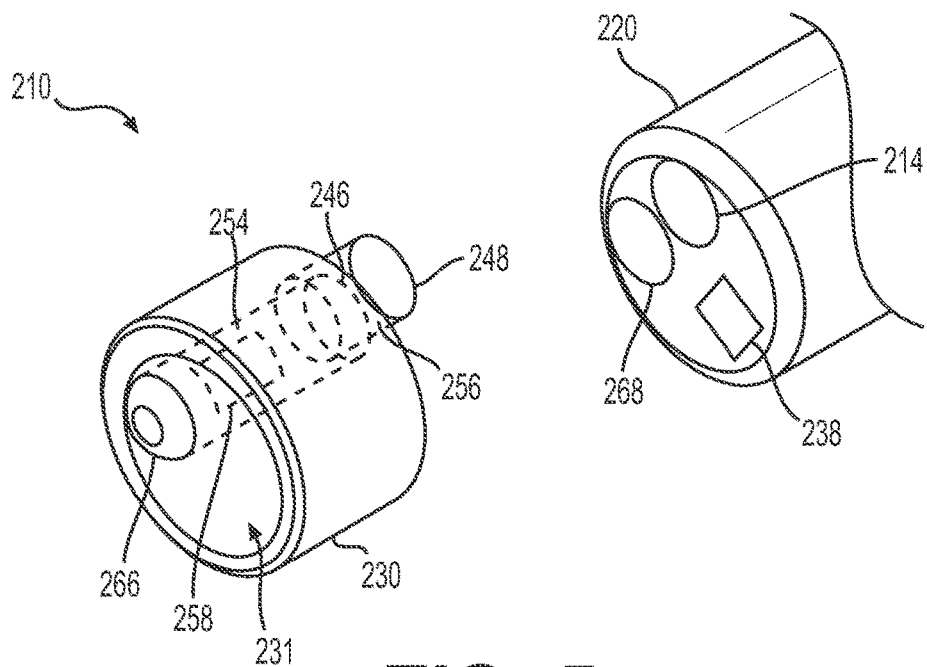
FIG. 5 illustrates a partially exploded view of a distal portion of another exemplary medical system, according to aspects of the present disclosure.

FIG. 5 illustrates an alternative example according to the present disclosure, with similar elements to medical system 10 shown by 200 added to the reference numbers. As shown, a distal portion of medical system 210 includes a delivery shaft 220 and an adaptor 230. Delivery shaft 220 includes a lumen 214, which may receive an energy delivery device (e.g., energy delivery device 26 described in connection with FIG. 1), irrigation fluid, or both. Delivery shaft 220 also includes a suction lumen 268. In this aspect, medical system 210 may include an insertion device similar to insertion device 12. A body of the insertion device may include two fluidly isolated (e.g., discrete) ports such that the energy delivery device 26 may be extended through lumen 214 and/or an irrigation source may be fluidly coupled to lumen 214 and the suction source may be coupled to suction lumen 268. Delivery shaft 220 may also include a visualization device or camera 238, and/or one or more illumination devices (not shown). Camera 238 and the one or more illumination devices may aid in the maneuvering of delivery shaft 220 and in the capture, dusting, and/or removal of one or more stones 5.

Adaptor 230 may be coupled to the distal end of delivery shaft 220 in any appropriate manner. Adaptor 230 includes a first coupling 246, for example, to fluidly couple adaptor 230 to suction lumen 268. Adaptor 230 also includes a second coupling 248, for example, to couple adaptor 230 to lumen 214. First coupling 246 is fluidly connected to a first coupling lumen 254, and second coupling 248 is connected to a second coupling lumen 256. First coupling lumen 254 may extend to distal end 266, which may be open or closed, as discussed above. First coupling lumen 254 also includes an aperture 258 fluidly connecting a portion of first coupling lumen 254 to a cavity 231 within adaptor 230. Second coupling lumen 256 may terminate proximally of the distal end of adaptor 230 and may be open to (e.g., communicate with) cavity 231.

In this aspect, suction may be applied through suction lumen 268 and first coupling lumen 254 to draw one or more stones 5 within cavity 231. Additionally, an energy delivery device (e.g., energy delivery device 26) may be inserted through lumen 214 and second coupling lumen 256. If the one or more stones 5 are small enough to pass through aperture 258, the one or more stones 5 may be removed through first coupling lumen 254 and suction lumen 268. If the one or more stones 5 are not small enough to pass through aperture 258, the energy delivery device 26 may deliver energy to break up or dust the stones 5 such that the stones 5 or stone dust 5A may be removed through first coupling lumen 254 and suction lumen 268. Irrigation fluid may be delivered through a sheath surrounding delivery shaft 220 or through an external lumen coupled to delivery shaft 220, as discussed above. Alternatively, irrigation fluid may be delivered around the energy delivery device 26 within lumen 214 and second coupling lumen 256.

Furthermore, as shown in FIG. 5, cavity 231 may extend through a length of adaptor 230 in order for camera 238 to visualize an area within and beyond adaptor 230. Alternatively or additionally, adaptor 230 may be formed of an at least partially transparent material. Moreover, based on the arrangement of first coupling 246 and second coupling 248 corresponding with the arrangement of lumen 214 and suction lumen 268, adaptor 230 may be accurately coupled to delivery shaft 220 without an alignment tool.

Figure 6:
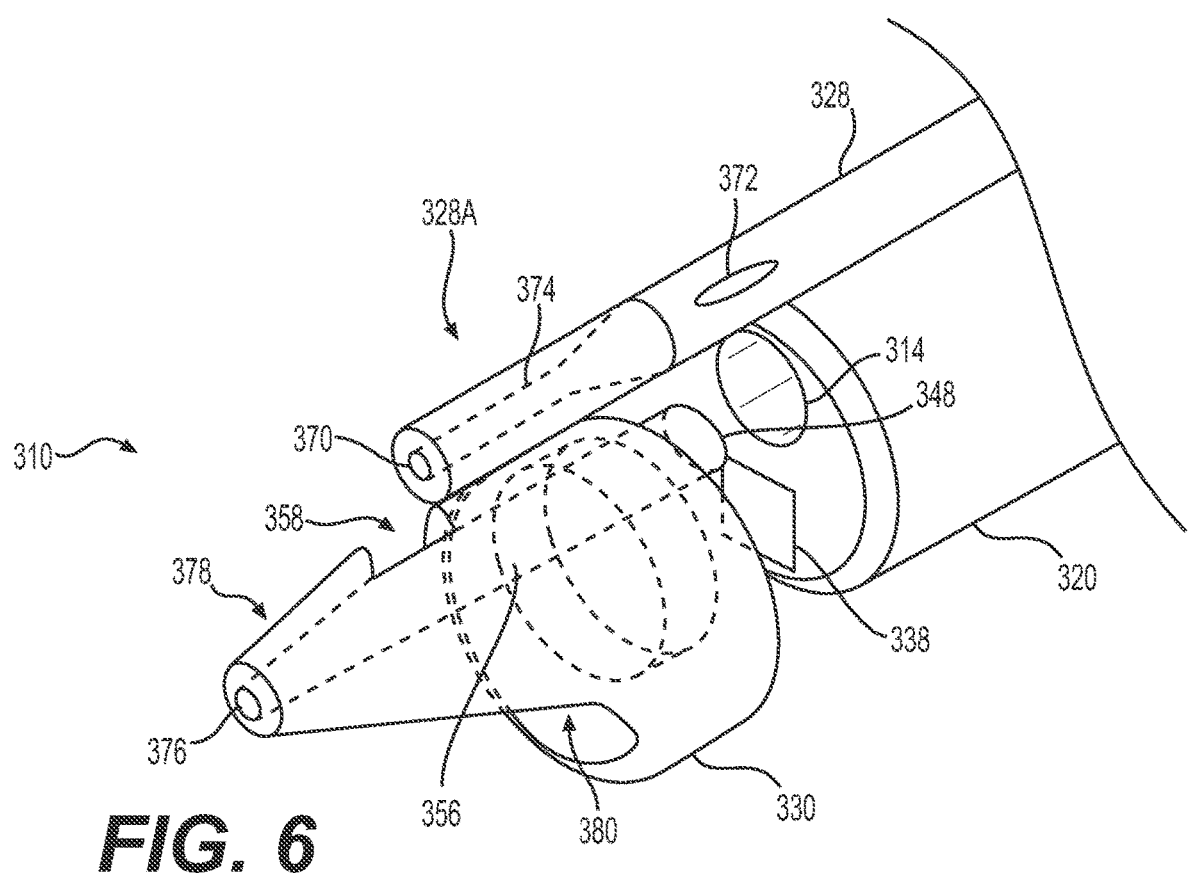
FIG. 6 illustrates a partially exploded view of a distal portion of an additional exemplary medical system, according to aspects of the present disclosure.

FIG. 6 illustrates an alternative example according to the present disclosure, with similar elements to medical system 10 shown by 300 added to the reference numbers. As shown, a distal portion of medical system 310 includes a delivery shaft 320, a tube 328, and an adaptor 330. It is noted that FIG. 6 illustrates a partially exploded view of the distal portion of medical system 310. Delivery shaft 320 includes a lumen 314 which may be coupled to a suction source, as discussed above. Delivery shaft 320 may also include a visualization device or camera 338, and may also include one or more illumination devices (not shown).

Tube 328 may be coupled to delivery shaft 320 via an adhesive or a sheath, as discussed above. Tube 328 may receive an energy delivery device, for example energy delivery device 26, through a hub or proximal connector, as discussed above. Tube 328 includes an open distal end 370. Tube 328 may also be coupled to an irrigation source. For example, the proximal hub or connector may be a Touhy-Borst adaptor or a one-way valve to form a seal around the energy delivery device and also allow for a controlled delivery of irrigation fluid through tube 328. Additionally, tube 328 may include one or more fluid delivery openings 372. Fluid delivery openings 372 may be proximal to distal end 370. Fluid delivery openings 372 may include a longitudinal length and a circumferential width along tube 328 such that irrigation fluid may be expelled through the one or more fluid delivery openings 372 rather than through distal end 370. In one aspect, fluid delivery openings 372 may include an opening smaller than a radial cross-section of the energy delivery device in order to help prevent the energy delivery device from inadvertently extending out of one of fluid delivery openings 372. Additionally, tube 328 may include an inner tapered portion 374. With the energy delivery device positioned within tube 328, tapered portion 374 may form an at least partial seal around the energy delivery device. Alternatively or additionally, although not shown, tube 328 may include an O-ring or other sealing element to form an at least partial seal around the energy delivery device.

Although not shown, in one aspect, a distal portion 328A of tube 328 may be a portion of adaptor 330, and tube 328 may be coupled to distal portion 328A via one or more couplings, as discussed above. Alternatively, distal portion 328A may be integrally (e.g., monolithically) formed with tube 328, and may align with adaptor 330, as shown in FIG. 6, based on the coupling of tube 328 to delivery shaft 220.

Adaptor 330 may be coupled to the distal ends of delivery shaft 320 and tube 328. Adaptor 330 includes a coupling 348, for example, to couple adaptor 330 to lumen 314. Coupling 348 is connected to a coupling lumen 356, which may extend distally beyond tube 328. Coupling lumen 356 also includes an aperture 358. Aperture 358 may be positioned to be aligned with or to extend distally beyond the distal end of tube 328. In this aspect, suction may be applied through lumen 314 and coupling lumen 356 to draw one or more stones 5 near the distal end of tube 328. Additionally, an energy delivery device may be inserted through tube 328. If the one or more stones 5 are small enough to pass through aperture 358, the one or more stones 5 may be removed through coupling lumen 356 and lumen 314. If the one or more stones 5 are not small enough to pass through aperture 358, the energy delivery device may deliver energy to break up or dust the stones 5 such that the stones 5 or stone dust 5A may be removed through coupling lumen 356 and lumen 314. Irrigation fluid may be delivered through tube 328 and out of the one or more fluid delivery openings 372, as discussed above.

Furthermore, coupling lumen 356 may extend to an open distal end 376. The open distal end 376 may be smaller than aperture 358, such that a majority of the suction applied through second coupling lumen 356 is applied through aperture 358. Coupling lumen 356 may include a distal taper 378 proximal to open distal end 376. In this aspect, a medical device, for example, a retrieval device may be extended through lumen 314 and coupling lumen 356 and out of open distal end 376. The distal taper 378 may help direct the medical device out of the open distal end 376.

Adaptor 330 may also include a visualization opening 380 that may extend through a length of adaptor 330, for example, below coupling 348 and lumen 356. When adaptor 330 is coupled to delivery shaft 320, visualization opening 380 may at least partial align with camera 338. Alternatively or additionally, adaptor 330 may be formed of an at least partially transparent material.

Figure 7:
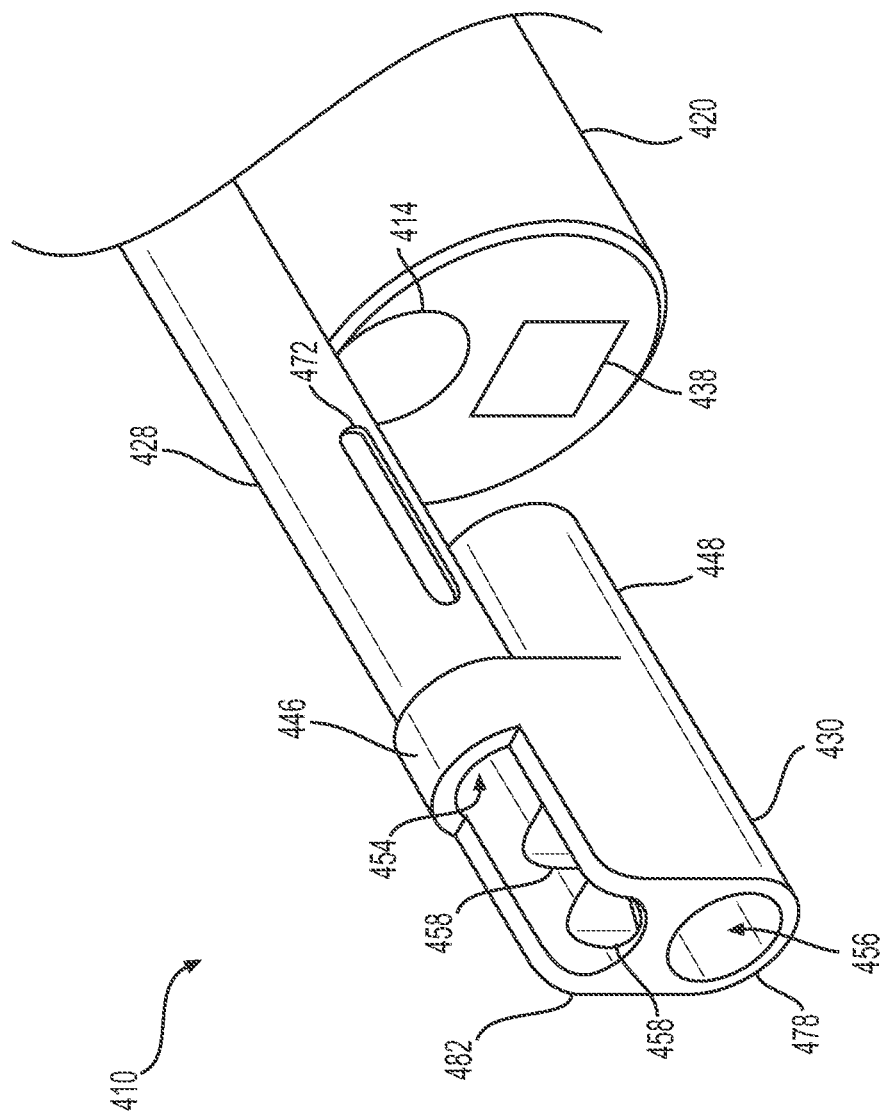
FIG. 7 illustrates a partially exploded view of a distal portion of a further exemplary medical system, according to aspects of the present disclosure.

FIG. 7 illustrates an alternative example according to the present disclosure, with similar elements to medical system 10 shown by 400 added to the reference numbers. As shown, a distal portion of medical system 410 includes a delivery shaft 420, a tube 428, and an adaptor 430. It is noted that FIG. 7 illustrates a partially exploded view of the distal portion of medical system 410. Delivery shaft 420 includes a lumen 414 which may be coupled to a suction source, as discussed above. Delivery shaft 420 may also include a visualization device or camera 438, and may also include one or more illumination devices (not shown).

Tube 428 may receive an energy delivery device, for example, through a hub or proximal connector as discussed above. Tube 428 includes an open distal end that is coupled to (and hidden in FIG. 7 by) adaptor 430. Tube 428 may also be coupled to an irrigation source, as discussed with respect to FIG. 6. Additionally, tube 428 may include one or more fluid delivery openings 472. Tube 428 may be coupled to delivery shaft 420 via an adhesive or a sheath, as discussed above.

Adaptor 430 may be coupled to the distal ends of delivery shaft 420 and tube 428. Adaptor 430 includes a first coupling 446, for example, to fluidly couple adaptor 430 to tube 428. Adaptor 430 also includes a second coupling 448, for example, to couple adaptor 430 to lumen 414. First coupling 446 is fluidly connected to a first coupling lumen 454, and second coupling 448 is connected to a second coupling lumen 456. First coupling lumen 454 may be fluidly connected to an open distal port 482. Open distal port 482 may include an opening in a distal end face of adaptor 430 and along a top longitudinal face of adaptor 430.

Second coupling lumen 456 may extend to a distal end 478 of adaptor 430. Second coupling lumen 456 also includes one or more apertures 458 fluidly connecting open distal port 482 to second coupling lumen 456. In this aspect, suction may be applied through lumen 414 and second coupling lumen 456 to draw one or more stones 5 near distal port 482. Additionally, an energy delivery device may be inserted through tube 428 and first coupling lumen 446. If the one or more stones 5 are small enough to pass through apertures 458, the one or more stones 5 may be removed through second coupling lumen 456 and lumen 414. If the one or more stones 5 are not small enough to pass through aperture(s) 458, the energy delivery device may deliver energy to break up or dust the stones 5 such that the stones 5 or stone dust 5A may be removed through second coupling lumen 456 and lumen 414. Irrigation fluid may be delivered through tube 428 and out of the one or more fluid delivery openings 472, as discussed above.

Moreover, second coupling lumen 456 may extend to open distal end 478. Open distal end 478 may be smaller than aperture(s) 458, such that a majority of the suction applied through second coupling lumen 456 is applied through aperture(s) 458. Furthermore, adaptor 430 may be positioned relative to camera 438 so as to not significantly impact the visualization of camera 438.

FIG. 8 illustrates an alternative example according to the present disclosure, with similar elements to medical system 10 shown by 500 added to the reference numbers. As shown, a distal portion of medical system 510 includes a delivery shaft 520, a tube 528, and an adaptor 530. It is noted that FIG. 8 illustrates a partially exploded view of the distal portion of medical system 510. Delivery shaft 520 includes a lumen 514 which may be coupled to a suction source, as discussed above. Delivery shaft 520 may also include a visualization device or camera 538, and may also include one or more illumination devices (not shown).

Tube 528 may receive an energy delivery device, for example, through a hub or proximal connector as discussed above. Tube 528 may be coupled to an irrigation source, and although not shown, tube 528 may include one or more fluid delivery openings proximal to adaptor 530, as discussed with respect to FIGS. 6 and 7.

Adaptor 530 may be coupled to the distal ends of delivery shaft 520 and tube 528, as discussed above. Adaptor 530 includes a first coupling lumen 554 connected to tube 528 and a second coupling lumen 556 connected to lumen 514. Although not shown, adaptor 530 may include first and second couplings to couple respective coupling lumens 554, 556 to tube 528 and lumen 514, as discussed above, for example, via a friction fit. Adaptor 530 may also include a visualization opening 580 that may extend through a length of adaptor 530, as discussed above.

In one aspect, first coupling lumen 554 extends to a closed distal end 566. Second coupling lumen 556 extends distally beyond first coupling lumen 554. Second coupling lumen 556 includes an open distal end 576. Second coupling lumen 556 may taper from the open distal end 576 to a narrower portion to form a cavity 531, with the narrower portion being approximately the same size as lumen 514. Additionally, adaptor 530 includes an aperture 558 connecting second coupling lumen 556 to first coupling lumen 554. In this aspect, suction may be applied through tube 528 and first coupling lumen 554 to draw one or more stones 5 near or into cavity 531 of adaptor 530. Furthermore, an energy delivery device may be inserted through lumen 514 and may face or extend into cavity 531. If the one or more stones 5 are small enough to pass through aperture 558, the one or more stones 5 may be removed through first coupling lumen 354 and tube 528. If the one or more stones 5 are not small enough to pass through aperture 558, the energy delivery device may deliver energy to break up or dust the stones 5 such that the stones 5 or stone dust 5A may be removed through first coupling lumen 554 and tube 528.

Adaptor 530 may include a distal portion 584, which may be narrower and/or smaller than the overall cross-sectional profile of medical device 510. Accordingly, distal portion 584 may help adaptor 530, and thus medical system 510, reach into smaller openings (e.g., lower calyxes in a kidney) to apply suction to stones 5, stone dust 5A, etc. Additionally, the taper within cavity 531 may help to funnel stones 5, stone dust 5A, or other particulate toward the energy delivery device positioned within lumen 514, which may more efficiently break up, fragment, or dust the stones 5, while also ensuring that the broken-up stones 5 or stone dust 5A are retained within cavity 531 in order to pass through aperture 558. Although not shown, cavity 531 may include an elliptical shape at distal end 576 and a round or circular shape at a proximal end so as to correspond with the shape of lumen 514 and/or the energy delivery device.

Figure 9A:
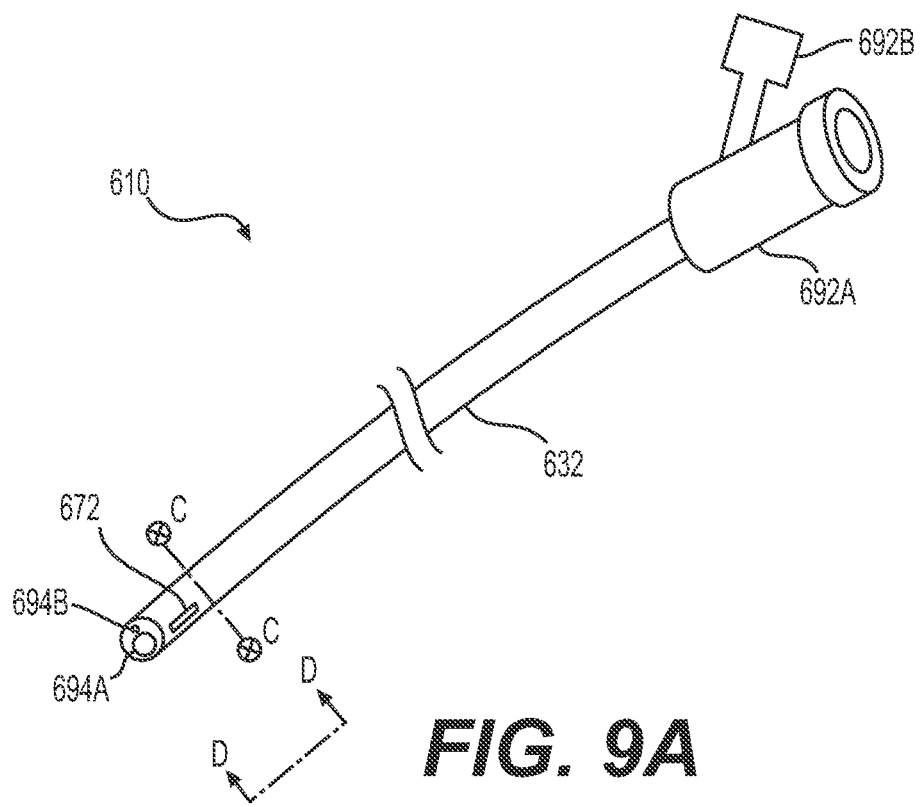
FIG. 9A illustrates another medical device, according to aspects of the present disclosure.
Figure 9B:
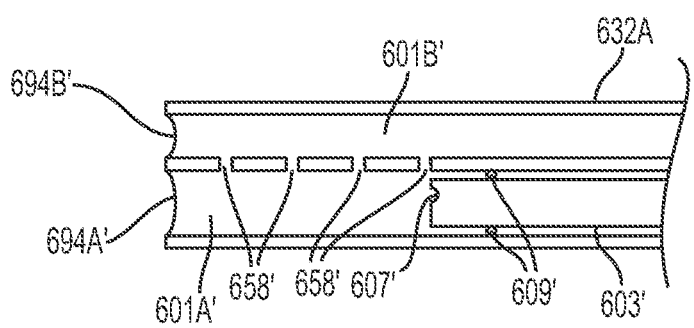
FIGS. 9B and 9C illustrate, respectively, cross-sectional views of exemplary configurations of the medical device of FIG. 9A, according to aspects of the present disclosure.
Figure 9C:
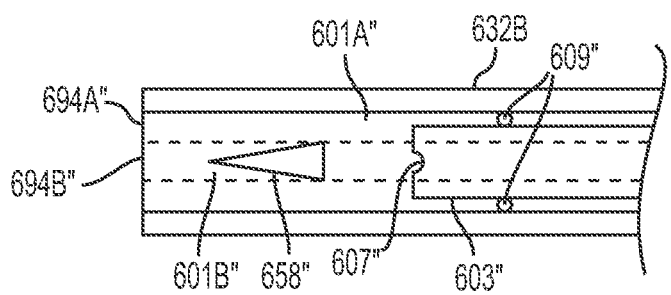

FIGS. 9A-9C illustrate an alternative example according to the present disclosure, with similar elements to medical system 10 shown by 600 added to the reference numbers. For example, a medical system 610 may include a sheath 632 with proximal connectors 692A and 692B. Sheath 632 may receive an insertion device and/or an energy delivery device (e.g., a laser fiber). For example, sheath 632 may include one or more internal lumens (not shown) connecting at least one of proximal connectors 692A, 692B to one or more distal openings 694A, 694B, respectively. Distal openings 694A, 694B may be different sizes than each other, approximately the same size, etc. Although not shown, distal openings 694A, 694B may be various shapes, for example, rectangular, half-moon or D-shaped, etc., in order to reduce the size of sheath 632. Moreover, one of distal openings 694A, 694B may be a first shape, and the other of distal openings 694A, 694B may be a second shape different from the first shape. Additionally, sheath 632 may include one or more fluid delivery openings 672.

Proximal connectors 692A, 692B may include one or more of a Touhy-Borst, a Gateway™ connector, a UroLock™ connector, a luer hub, or another appropriate connector. For example, one or more of proximal connectors 692A, 692B may be a Touhy-Borst connector, which may include a grommet within the connector that may be tightened to compress around a shaft of an insertion device or an energy delivery device to form a seal and/or to lock the insertion device or the energy delivery device in place relative to sheath 632.

In one aspect, a first lumen connecting to distal opening 694A may receive an insertion device. A second lumen connecting to distal opening 694B may be receive one or more medical devices and/or be used to apply suction to an area surrounding distal opening 694B. The insertion device and/or the medical devices may be longitudinally movable within respective lumens of sheath 632, for example, to extend distally out of distal openings 694A, 694B, and/or be retracted proximally within distal openings 694A, 694B. Additionally, sheath 632 may include one or more fluid delivery openings 672 to deliver fluid to a body cavity through one or more lumens, for example, radially around one or more of the insertion device or the medical device.

FIG. 9B illustrates an exemplary cross-sectional arrangement of sheath 632, taken along line C, and depicted as sheath 632A. As shown, sheath 632A includes a first lumen 601A' and a second lumen 601B', respectively coupled to openings 694A' and 694B'. First lumen 601A' may receive an insertion device 603', which may include a device lumen 607' (e.g., for a working channel to receive an energy delivery device), as discussed above. First lumen 601A' may include one or more O-rings 609' to form a seal around insertion device 603'. Sheath 632A may also include one or more apertures 658' connecting first lumen 601A' to second lumen 601B'. In one aspect, an energy delivery device may be inserted through device lumen 607', and suction may be applied through second lumen 601B'. Opening 694B' may be intentionally blocked by a large stone, or sheath 632A may include another element to occlude or close opening 694B'. In this aspect, the energy delivery device and the applied suction may help to dust and remove stones 5, with only small stones 5 or stone dust 5A passing through apertures 658'. Additionally, although not shown, one or more fluid delivery openings may be arranged along first lumen 601A' proximal of the one or more O-rings 609'. In this manner, irrigation fluid may be delivered from first lumen 601A' to a body cavity.

FIG. 9C illustrates an exemplary cross-sectional arrangement of sheath 632, taken along line D, and depicted as sheath 632B. As shown, sheath 632B includes a first lumen 601A" and a second lumen 601B", respectively coupled to openings 694A" and 694B". In the arrangement shown, first lumen 601A' is positioned in front of second lumen 601B" in a direction normal to the plane of the paper. For example, first lumen 601A" may be physically separated from second lumen 601B" by a wall or by a solid internal portion of sheath 632B. First lumen 601A" may receive an insertion device 603", which may include a device lumen 607" (e.g., for a working channel to receive an energy delivery device), as discussed above. First lumen 601A" may include one or more O-rings 609" to form a seal around insertion device 603". Sheath 632B may also include one or more apertures 658" fluidly connecting first lumen 601A" to second lumen 601B". As shown, the one or more apertures 658" may be include a narrow distal portion and a wider proximal portion, for example, to form a triangular or tapered shape. Nevertheless, this disclosure is not so limited, as the one or more apertures 658" may include one or more other shapes.

In one aspect, an energy delivery device may be inserted through device lumen 607", and suction may be applied through second lumen 601B". Opening 694B" may be intentionally blocked by a large stone, or sheath 632B may include another element to occlude or close opening 694B". In this aspect, the energy delivery device and the applied suction may help to dust and remove stones, with only small stones 5 or stone dust 5A passing through apertures 658". Additionally, smaller stones 5 or stone dust 5A may pass through the narrower, distal portion of the one or more apertures 658", and larger stones 5B (still small enough to pass through second lumen 601B") may be broken-up with the delivered energy and pass through the larger, proximal portion of the one or more apertures 658". Furthermore, although not shown, one or more fluid delivery openings may be arranged along first lumen 601A" proximal of the one or more O-rings 609". In this manner, irrigation fluid may be delivered from first lumen 601A" to a body cavity.

Figure 10A:
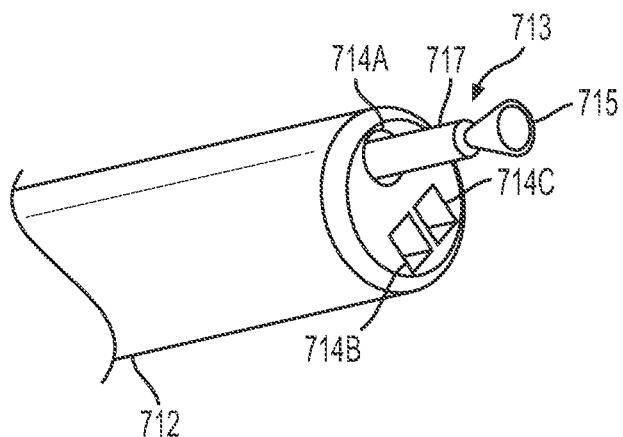
FIGS. 10A-10C illustrate various additional medical devices that may be used in conjunction with the medical systems disclosed herein, according to aspects of the present disclosure.
Figure 10B:
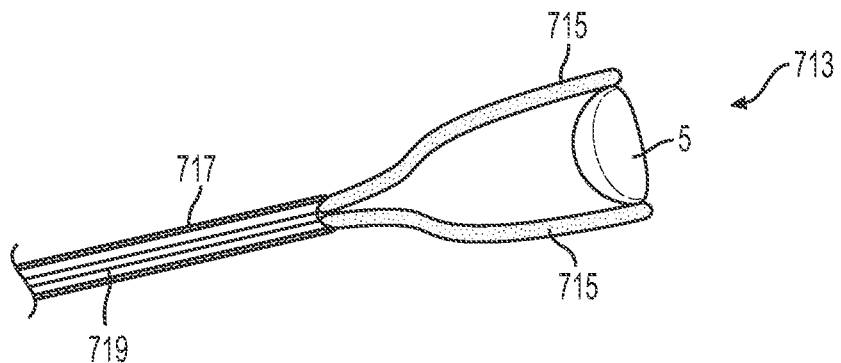
Figure 10C:
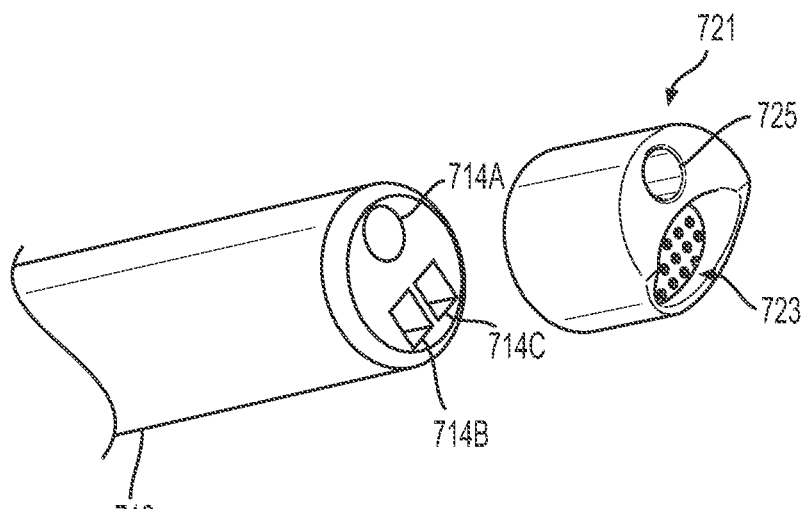

FIGS. 10A-10C illustrate various components or medical devices that may be coupled to one or more insertion devices 712, similar to insertion device 12. Although not shown, insertion device 712 may be delivered through a sheath and/or coupled to an adaptor, as discussed above.

As shown in FIGS. 10A and 10C, insertion device 712 may include a plurality of lumens 714A, 714B, and 714C. In one aspect, one or more of a camera or an illumination source may be positioned within one or more of lumens 714A, 714B, 714C. Alternatively or additionally, one or more of lumens 714A, 714B, 714C may connect a distal portion of insertion device 712 to a proximal portion of insertion device 712.

FIGS. 10A and 10B illustrate a retrieval device 713. As shown in FIG. 10A, retrieval device 713 may be positioned within lumen 714A. Retrieval device 713 may include an expandable distal portion 715, which may be formed of an expandable and collapsible material. For example, distal portion 715 may be formed of a semi-permeable membrane material. When a sheath 717 is retracted proximally, distal portion 715 may expand. In such arrangements, distal portion 715 may be biased toward an expanded configuration. Moreover, suction may be applied through lumen 714A and/or through a device lumen 719 (FIG. 10B) in order to capture one or more stones 5. Once the one or more stones 5 are captured within distal portion 715, retrieval device 713 may be collapsed, e.g., by extending sheath 717 distally or retracting distal portion 715 proximally, and retrieval device 713 may be removed from the body cavity. In one aspect, retrieval device 713 with the captured stone 5 may be removed through lumen 714A without removing insertion device 712.

Alternatively or additionally, distal portion 715 may include a filter element that may be selectively deployed and/or collapsed, for example, self-expanding when extended distally out of lumen 714A. In one aspect, distal portion 715 may be extended and deployed, and then retracted proximally to at least partially block lumen 714A. With suction applied through lumen 714A, one or more stones 5 may be captured in distal portion 715. Depending on the size of the captured stones 5, distal portion 715 may be removed from lumen 714A to remove the captured stones 5. Moreover, although not shown, distal portion 715 may include an controllable ring or other element at a distal end, and a user may actuate the controllable ring to at least partially close the distal end of distal portion 715, which may help retain any captured stones 5. The user may remove, move, break-up, dust, or otherwise treat the captured stones 5. Furthermore, distal portion 715 may include a substance, fluid coating, or mesh on or within the internal walls. For example, distal portion 715 may include corn starch or another substance that may constrict around or bind to any stones 5 within distal portion 715. The stones 5 may be retained within distal portion 715, and the user may remove, move, break-up, dust, or otherwise treat the captured stones 5.

In another aspect shown in FIG. 10C, a distal cap 721 may be coupled to a distal end of insertion device 712. Distal cap 721 may include a filter portion 723, and a filter-free portion or an opening 725. For example, when distal cap 721 is coupled to the distal end of insertion device 712, filter portion 723 may partially occlude lumens 714B and 714C. Additionally, when distal cap 721 is coupled to the distal end of insertion device 712, opening 725 may align with lumen 714A. As such, an energy delivery device may be delivered through lumen 714A and opening 725 to deliver energy to break up or dust one or more stones or other hardened masses. Then, suction may be applied through one or more of lumens 714B or 714C to remove portions of the broken-up stones or hardened masses. Similar to the apertures discussed above, filter portion 723 may control the size of the broken-up stones or hardened masses that may pass through filter portion 723 and one or more of lumens 714B or 714C. Moreover, in one aspect, irrigation fluid may be delivered through one of lumens 714A, 714B, or 714C in order to maintain a pressure, volume, or other detail within the body cavity. The irrigation fluid may pass through the filter portion 723.

It is noted that the arrangements shown in FIGS. 10A-10C may be modified to be incorporated with the adaptors discussed in FIGS. 1-8 and 9A-9C. For example, retrieval device 713 may be inserted through a tube or delivery shaft of the medical systems of FIGS. 1-8. Alternatively or additionally, distal cap 721 may be coupled to a distal end of one of the adaptors of FIGS. 1-9.

Figure 11:
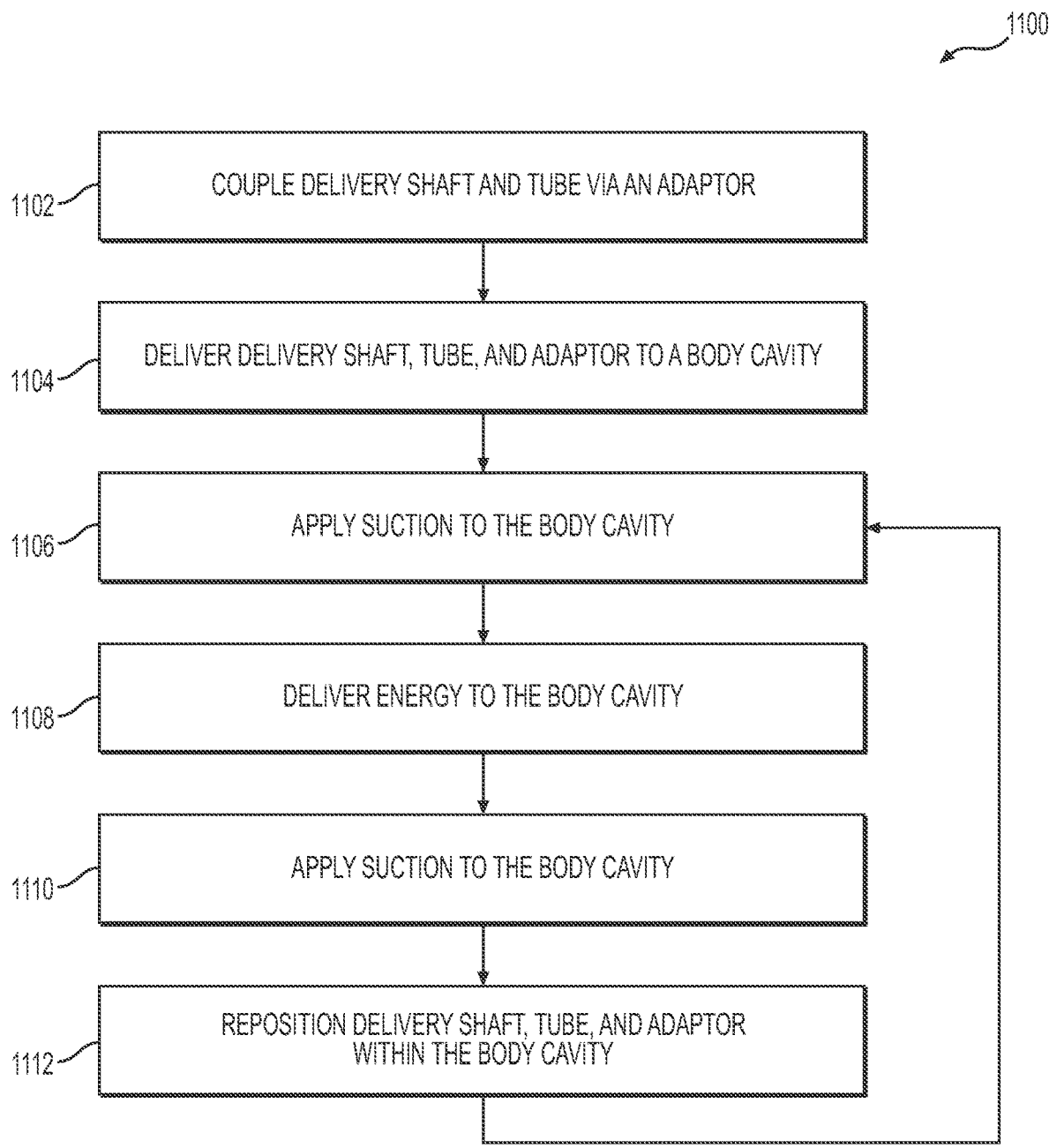
FIG. 11 provides a flowchart depicting an exemplary method for breaking up and removing a hardened mass from a body cavity, according to aspects of the present disclosure.

FIG. 11 depicts a flow diagram of a method 1100 that may be performed with any of the medical devices and systems discussed herein. For example, a step 1102 includes coupling a delivery shaft 20 and a tube 28 via an adaptor 30. As discussed, coupling delivery shaft 20 and tube 28 via adaptor 30 may include a friction fit, a sheath, an adhesive, a loop of material, etc. A step 1104 includes delivering delivery shaft 20, tube 28, and adaptor 30 to a body cavity. Delivering the coupled elements to a body cavity may include inserting delivery shaft 20, tube 28, and adaptor 30 through an access sheath (e.g., sheath 32). Additionally or alternatively, delivering the coupled elements to a body cavity may include positioning a guidewire through one or more of the tubes or lumens in delivery shaft 20, and advancing medical system 10 along the guidewire to the body cavity. Once delivery shaft 20, tube 28, and adaptor 30 are positioned within the body cavity, the guidewire may be removed, for example, via port 24.

Next, a step 1106 includes applying suction to the body cavity. As discussed herein, the suction may be applied via either the tubes or the delivery shafts. In one aspect, hub 29 of tube 28 may be coupled to a suction source. The applied suction may draw one or more stones 5 or stone dust 5A into cavity 31. Small stones and stone dust 5A may pass through aperture 58 and be removed through tube 28. Additionally, large stones 5B may be secured within cavity 31, for example, secured against aperture 58. In one aspect, applying suction to the body cavity may help the user capture and move one or more large stones 5B or even larger stones 5C, for example, to another portion of the body cavity.

A step 1108 includes delivering energy to the body cavity. As discussed herein, the energy may be delivered via either the tubes or the delivery shafts. In one aspect, energy delivery device 26 may extend through lumen 14 in delivery shaft 20 to a position aligned with distal end 36, just proximal to distal end 36, or just distal to distal end 36. In another aspect, energy delivery device 26 may extend distal to cavity 31. Delivering energy from delivery device 26 may fragment, dust, or otherwise break up the one or more large stones 5B secured against aperture 58 and/or the one or more even larger stones 5C secured against distal rim 33. Additionally, in one aspect, suction may be applied during the energy delivery to remove fragments of large stones 5B through aperture 58 and/or to help retain large stones 5B against aperture 58. Moreover, suction may be applied during the energy delivery to remove fragments of even larger stones 5C through aperture 58 and/or to help retain the even larger stones 5C against distal rim 33.

Next, a step 1110 includes again applying, initiating, or maintaining suction to the body cavity. The applied suction may help to urge fragments of stones 5 or stone dust 5A through aperture 58 and proximally tube 28. In one aspect, if suction was also applied during the energy delivery in step 1108, a greater amount of suction may be delivered in step 1110.

An optional step 1112 includes repositioning delivery shaft 20, tube 28, and adaptor 30 within the body cavity. For example, deflection lever 22 may be used to reposition delivery shaft 20, tube 28, and adaptor 30 to another location within the body cavity, and steps 1106-1112 may be repeated as many times as necessary to complete a stone removal procedure. Once the stone(s) or other material has been removed from the treatment site, which may be confirmed via camera 38 or other such imaging modalities or visual inspection methods, the operator may remove medical system 10 from the body cavity. Alternatively, if step 1110 concludes the stone removal procedure 1100, suction may be applied to retain a large stone 5B or other materials within or against cavity 31, and medical system 10 may be removed from the body cavity.

The systems, devices, and methods discussed herein may help an operator to quickly and safely deliver medical treatment to a treatment site, for example, to break up and remove kidney stones or other hardened masses. As discussed above, once medical system 10 is positioned at the treatment site, there is no need to remove insertion device 12, energy delivery device 26, or tube 28 to deliver fluid, delivery energy, apply suction, or otherwise treat the treatment site within the body cavity.

As mentioned above, adaptors 30, 130, 230, 330, 430, 530 may be formed by additive manufacturing, which may help form the respective lumens, apertures, cavities, etc. Moreover, in some aspects, a user may intentionally block or clog an open distal end of the tube or the adaptor in order to trap stones 5 or stone dust 5A, and/or in order to direct suction through the apertures.

Additionally, different adaptors and different arrangements of one or more tubes may be appropriate for different insertion devices or delivery shafts. For example, a delivery shaft with a single lumen or working channel may require an adaptor and tube arrangement as discussed with respect to FIGS. 1-3 and 6-8. On the other hand, a delivery shaft with two lumens or working channels may require an adaptor arrangement as discussed with respect to FIG. 4. Additionally, the number, size, and/or location of the one or more stones or hardened masses that are to be retrieved, dusted, and/or removed may affect which of the various arrangements discussed herein is the most appropriate. For example, if the one or more stones are located in a smaller or lower calyx, the arrangement shown and discussed with respect to FIG. 8 may be appropriate in order for the smaller distal end 576 to reach the one or more stones. Furthermore, if one or more stones are to be captured before a stone dusting procedure, a user may deliver one or more grasping or basket devices to capture and/or remove the one or more stones before the stone dusting procedure, as discussed with respect to FIGS. 10A-10C.

The adaptors and tubes may be used with a disposable or re-usable insertion device to break up and remove one or more stones or hardened masses, with a reduced likelihood of clogging during removal. Additionally, a single user may be able to use the medical systems discussed herein to reposition or remove stones or stone fragments without the need for a basket or other retrieval device. The adaptors may allow for applied suction to capture the stone(s) during lithotripsy, and the cavity within an adaptor may contain the stone(s) or stone fragments. The applied suction, delivered irrigation, and/or delivered energy may be controlled by the user, for example, via one or more foot pedals, triggers, user interface, switches, fluid management systems, etc.

The one or more apertures within the adaptors may be used to size the stones and/or stone dust. For example, stones or stone dust that may pass through the one or more apertures are small enough to travel proximally through the suction tube or channel to be removed and/or collected. Stones or stone dust that are not able to pass through the one or more apertures may be held in place against the one or more apertures by the suction in a position aligned with a distal end of the energy delivery device, which may then be used to dust, fragment, or otherwise break up the larger stones such that the broken-up stones may then pass through the one or more apertures and through the suction tube or channel. Additionally, in examples where the stone fragments or dust are removed through an external tube, there is no risk of the stone fragments or dust scratching or damaging an interior working channel of a reusable insertion device.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical system, comprising:
   an insertion device including a delivery shaft with at least one lumen;
   a tube coupled to an exterior of the delivery shaft, wherein the tube includes a lumen; and
   an adaptor coupling a distal end of the delivery shaft to a distal end of the tube, the adaptor comprising a first lumen coupled to the lumen of the tube and a second lumen coupled to the lumen of the delivery shaft,
   wherein one of the delivery shaft and the tube is configured to receive an energy delivery device,
   wherein the other of the delivery shaft and the tube is configured to be coupled to a suction source to apply suction,
   wherein the first lumen of the adaptor is connected to the second lumen of the adaptor via at least one aperture, and
   wherein the aperture includes a screen, a mesh, a strainer, a sieve, a filter, or a sifter.

2. The medical system of claim 1, wherein a central longitudinal axis of the lumen of the tube is parallel to a central longitudinal axis of a lumen of the delivery shaft.

3. The medical system of claim 1, wherein the aperture includes an opening that is smaller than a cross-sectional area of one of the lumen of the tube or the lumen of the delivery shaft, and wherein the tube includes one or more fluid delivery openings located proximal to a coupling with the adaptor.

4. The medical system of claim 1, wherein at least one lumen of the adaptor includes a proximally tapered cross-section.

5. The medical system of claim 1, wherein the tube is coupled to the delivery shaft via an outer sheath.

6. The medical system of claim 1, wherein the tube is coupled to the delivery shaft via an adhesive.

7. The medical system of claim 1, wherein the adaptor is coupled to the distal ends of the delivery shaft and the tube via a friction fit.

8. The medical system of claim 1, wherein the delivery shaft includes a visualization device.

9. The medical system of claim 8, wherein the adaptor includes a visualization opening at least partially aligned with the visualization device.

10. The medical system of claim 1, wherein the adaptor is formed of an at least partially transparent material.

11. The medical system of claim 1, further comprising a retrieval device configured to be positioned within either the lumen of the delivery shaft or the lumen of the tube.

12. The medical system of claim 1, further comprising an end cap with a filter portion and an opening.

13. An adaptor for a medical system, comprising:
   a first coupling portion configured to couple a tube to a first lumen of the adaptor;
   a second coupling portion configured to couple a delivery shaft to a second lumen of the adaptor; and
   an aperture fluidly connecting the first lumen to the second lumen,
   wherein the first lumen and the second lumen are parallel, wherein the first lumen of the adaptor is connected to the second lumen of the adaptor via at least one aperture, and wherein the aperture includes a screen, a mesh, a strainer, a sieve, a filter, or a sifter.

14. The adaptor of claim 13, wherein the first lumen includes a closed distal end, and wherein the second lumen includes an open distal end defining a cavity.

15. The adaptor of claim 14, wherein the cavity of the second lumen is proximally tapered, and wherein a proximal portion of the cavity is adjacent to the aperture.

16. A method, comprising:
coupling a distal end of a delivery shaft to a distal end of a tube via an adaptor, the adaptor comprising a first lumen coupled to the lumen of the tube and a second lumen coupled to the lumen of the delivery shaft;
delivering the delivery shaft, the tube, and the adaptor to a body cavity;
applying suction to the body cavity through a lumen of the delivery shaft or a lumen of the tube to remove an object via an aperture within the adaptor or to retain the object adjacent to the aperture within the adaptor; and
delivering energy to the body cavity through the lumen of the delivery shaft or the lumen of the tube
wherein the first lumen of the adaptor is connected to the second lumen of the adaptor via at least one aperture, and
wherein the aperture includes a screen, a mesh, a strainer, a sieve, a filter, or a sifter.

17. The method of claim 16, wherein the step of delivering the delivery shaft, the tube, and the adaptor to the body cavity includes positioning a guidewire within the lumen of at least one of the delivery shaft or the tube and advancing at least one of the delivery shaft, the tube, and the adaptor along the guidewire,
wherein the step of delivering energy to the body cavity further includes applying suction to the body cavity; and
wherein the method further comprises repositioning the delivery shaft, the tube, and the adaptor to another position within the body cavity and repeating the apply suction step and the energy delivery step.

* * * * *